(12) United States Patent
Maleczka, Jr. et al.

(10) Patent No.: US 6,958,420 B2
(45) Date of Patent: Oct. 25, 2005

(54) SYNTHESIS OF AMINOARYLBORONIC ESTERS AND SUBSTITUTED ANILINES FROM ARENES VIA CATALYTIC C-H ACTIVATION/BORYLATION/AMINATION AND USES THEREOF

(75) Inventors: Robert E. Maleczka, Jr., DeWitt, MI (US); Milton R. Smith, III, East Lansing, MI (US); Daniel Holmes, DeWitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 217 days.

(21) Appl. No.: 10/623,196

(22) Filed: Jul. 18, 2003

(65) Prior Publication Data

US 2004/0024237 A1 Feb. 5, 2004

Related U.S. Application Data

(60) Provisional application No. 60/397,369, filed on Jul. 19, 2002.

(51) Int. Cl.$^7$ ................................................. C07F 5/02

(52) U.S. Cl. ........................................................ 568/6

(58) Field of Search ............................................. 568/6

(56) References Cited

FOREIGN PATENT DOCUMENTS

| WO | WO 2000015213 | * | 3/2000 |
| WO | WO 2000077001 | * | 12/2000 |
| WO | WO 2001010868 | * | 2/2001 |
| WO | WO 2001097786 | * | 12/2001 |

OTHER PUBLICATIONS

Staab.Heinx A. et al Justus Liebigs Annalen de Chemie (1971), 753, 80–91.*

Klis, Tomasz et al , Main Group Metal Chemistry (20020 25 (8), 479–484.*

* cited by examiner

Primary Examiner—Paul J. Killos
(74) Attorney, Agent, or Firm—Ian C. McLeod

(57) ABSTRACT

A process is described for synthesizing aminoarylboronic esters of the general formula

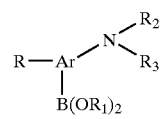

wherein R, $R_2$, and $R_3$ are each an alkyl, aryl, vinyl, alkoxy, carboxylic esters, amides, or halogen; Ar is any variety of phenyl, naphthyl, anthracyl, heteroaryl; and $R_1$ is alkyl, hydrogen, or aryl. The aminoarylboronic esters are produced via the metal-catalyzed coupling of arylboronic esters of the general formula

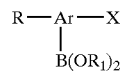

wherein R and $R_1$ are any non-interfering group and X is chloro, bromo, iodo, triflates, or nonaflates to amines (primary and secondary). In particular, a process is described for the synthesis of the aminoarylboronic esters via a stepwise or tandem process in which one catalytic event is a metal-catalyzed borylation and the other catalytic event is a metal-catalyzed amination.

92 Claims, 2 Drawing Sheets

16  17  18

19  21  20

22  23  24

25  26  27

Figure 1:
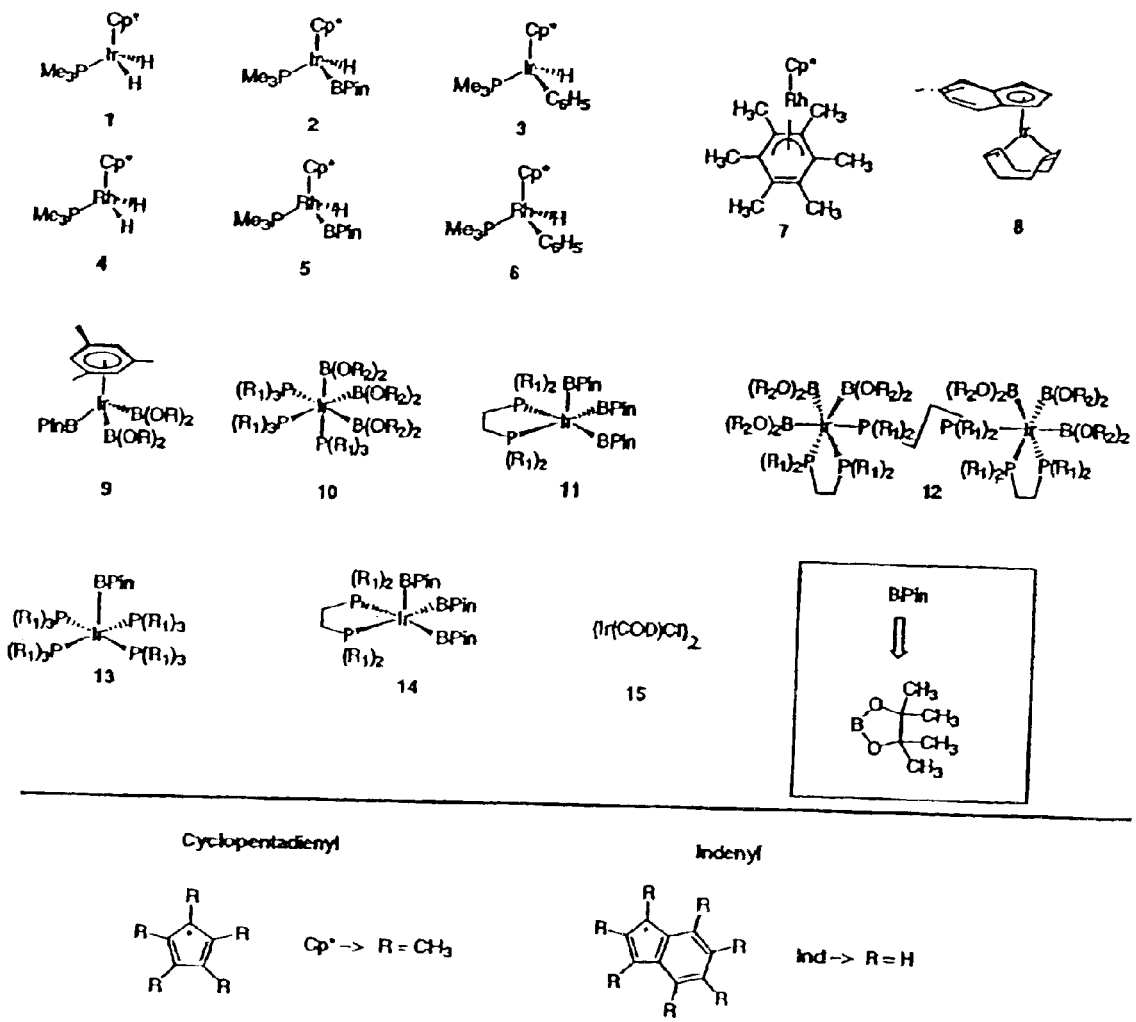

SYNTHESIS OF AMINOARYLBORONIC ESTERS AND SUBSTITUTED ANILINES FROM ARENES VIA CATALYTIC C-H ACTIVATION/BORYLATION/AMINATION AND USES THEREOF

CROSS-REFERENCE TO RELATED APPLICATION

This application claims priority to U.S. Provisional Patent Application No. 60/397,369, filed Jul. 19, 2002.

STATEMENT REGARDING FEDERALLY SPONSORED RESEARCH OR DEVELOPMENT

Not applicable

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a process for synthesizing aminoarylboronic esters of the general formula

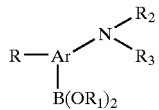

wherein R, $R_2$, and $R_3$ are each independently an alkyl, aryl, vinyl, alkoxy, carboxylic esters, amides, or halogen; Ar is any variety of phenyl, naphthyl, anthracyl, heteroaryl; and $R_1$ is alkyl, hydrogen, or aryl. The aminoarylboronic esters are produced via the metal-catalyzed coupling of arylboronic esters of the general formula

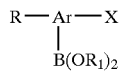

wherein R and $R_1$ are any non-interfering group and X is chloro, bromo, iodo, triflates, or nonaflates to amines (primary and secondary). In particular, the present invention provides a process for the synthesis of the aminoarylboronic esters via a step-wise or tandem process in which one catalytic event is a metal-catalyzed borylation and the other catalytic event is a metal-catalyzed amination.

(2) Description of Related Art

There is no single method established for the synthesis of aminoarylboronic esters in the prior art. The most common method involves the derivatization of 3-aminophenylboronic acid (See for a recent example; Gravel et al., J. Org. Chem. 67: 3 (2002)), which in turn was originally synthesized from 3-bromonitrobenzene via (i) grignard formation, (ii) reaction with a alkylborate followed by hydrolysis, (iii) and reduction of the nitro group (See, Bean and Johnson, J. Am. Chem. Soc. 54: 4415 (1932)).

Therefore, there remains a need for a process for synthesizing aminoarylboronic esters and substituted anilines from arenes that is safer and less laborious than the prior art methods.

SUMMARY OF THE INVENTION

The present invention provides a process for synthesizing aminoarylboronic esters of the general formula

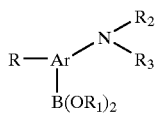

wherein R, $R_2$, and $R_3$ are each an alkyl, aryl, vinyl, alkoxy, carboxylic esters, amides, or halogen; Ar is any variety of phenyl, naphthyl, anthracyl, heteroaryl; and $R_1$ is alkyl, hydrogen, or aryl. The aminoarylboronic esters are produced via the metal-catalyzed coupling of arylboronic esters of the general formula

wherein R and $R_1$ are any non-interfering group and X is chloro, bromo, iodo, triflates, or nonaflates to amines (primary and secondary). In particular, the present invention provides a process for the synthesis of the aminoarylboronic esters via a step-wise or tandem process in which one catalytic event is a metal-catalyzed borylation and the other catalytic event is a metal-catalyzed amination.

Therefore, the present invention provides a process for producing an aminoarylboronic ester which comprises (a) reacting an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands, preferably under anhydrous conditions, to produce an arylboronic ester; and (b) aminating the arylboronic ester with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester.

The present invention further provides a process for producing an aminoarylboronic ester which comprises (a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands, preferably under anhydrous conditions, to produce an arylboronic ester; and (b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester.

The present invention further provides a process for C—N coupling an aryl halide to an aminoarylboronic ester via the amine functionality of the aminoarylboronic ester which comprises (a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands, preferably under anhydrous conditions, to produce an arylboronic ester; (b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester; and (c) reacting the aminoarylboronic ester with the aryl halide in the presence of a palladium metal catalyst complex in the presence of water to couple the aryl halide to the aminoarylboronic ester.

The present invention further provides a process for C—C coupling an aryl halide to an aminoarylboronic ester via the borane functionality of the aminoarylboronic ester which comprises (a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands, preferably under anhydrous conditions, to produce an arylboronic ester; (b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester; and (c) reacting the aminoarylboronic ester with the aryl halide in the presence of a palladium metal catalyst complex in the presence of water to couple the aryl halide to the aminoarylboronic ester.

The present invention further provides a process for producing an aminoarylboronic ester which comprises reacting an arylboronic ester with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester.

The present invention further provides a process for producing a substituted phenol amine which comprises (a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands under anhydrous conditions to produce an arylboronic ester; (b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce an aminoarylboronic ester; and (c) oxidizing the aminoarylboronic ester with a hydrogenating oxidizing compound to produce the substituted phenol amine.

In a further embodiment of the above processes, iridium complex is selected from the group consisting of ((COD)Ir(OCH$_3$))$_2$, (Cp*)Ir(H)$_2$(Me$_3$P), (Cp*)Ir(H)(BPin)(Me$_3$P), (Cp*)Ir(H)(C$_6$H$_5$)(Me$_3$P), (Ind)Ir(COD), (Ind)Ir(dppe), (MesH)Ir(BPin)(B(OR)$_2$)$_2$, ((R$_1$)$_3$P)$_3$Ir(B(OR$_2$)$_2$)$_3$, (R$_1$)$_2$P)$_2$Ir(BPin)$_3$, (((R$_1$)$_2$P)$_3$Ir((R$_2$O)$_2$B)$_3$)$_2$, ((R$_1$)$_3$P)$_4$Ir(BPin), ((R$_1$)$_3$P)$_2$Ir(BPin)$_3$, (MesH)Ir(BPin)$_3$, and (IrCl(COD))$_2$, (PMe$_3$)$_2$IrH$_5$, ((R$_1$)$_3$P)$_2$IrH$_5$, and ((R)$_3$P)$_2$IrH$_x$(B(OR$_2$)$_2$)$_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, R$_1$, and R$_2$ are hydrogen, linear or branched alkyl containing 1 to 8 carbons, aryl, or a carbon in a cyclic structure.

In a further embodiment of the above processes, the iridium complex is (Ind)Ir(COD) or ((COD)Ir(OCH$_3$))$_2$ wherein Ind is indenyl and COD is 1,5-cyclooctadiene.

In a further embodiment of the above processes, the organic ligand is a phosphorus organic ligand selected from the group consisting of trimethyl phosphine (PMe$_3$), 1,2-bis (dimethylphosphino)ethane (dmpe), and 1,2-bis (diphenylphosphino)ethane (dppe). In other embodiments, the organic ligand is a nitrogen ligand selected from the group consisting of 2,2'-dipyridyl and 4,4'-di-tert-butyl-2,2'-dipyridyl.

In a further embodiment of the above processes, the borane is pinacolborane (BPin).

In a further embodiment of the above processes, the metal catalyst is palladium.

In a further embodiment of the above processes, the metal catalyst complex is selected from Pd(PPh$_3$)$_4$, Pd$_2$(dba)$_3$/P($^t$Bu)$_3$, PdCl$_2$(dppf), and Pd(OAc)$_2$/Cy$_3$P wherein P is phosphorus and Ph is phenyl, dba is dibenzylideneacetone, $^t$Bu is tert-butyl, dppf is diphenylphosphinoferrocene.

In a further embodiment of the above processes, wherein the aryl compound has the formula (R)Ar(X), the arylboronic ester has the formula (R)Ar(X)B(OR$_1$)$_2$, and the aminoarylboronic ester has the formula (R)Ar(NR$_2$R$_3$)B(OR$_1$)$_2$ wherein R, R$_2$, and R$_3$ are each any non-interfering group, preferably a group selected from the group consisting of alkyl, aryl, vinyl, alkoxy, carboxylic esters, amides, and halogen; Ar is selected from the group consisting of phenyl, naphthyl, anthracyl, and heteroaryl; X is a halogen or pseudohalogen preferably selected from the group consisting of chloro, bromo, iodo, triflates, and nonaflates; and R$_1$ is any non-interfering group, preferably a group selected from the group consisting of alkyl, hydrogen, and aryl.

In particular embodiments of the above borylation reactions, the molar ratio of the aryl compound to the borane is between about 10 to 1 and 1 to 10, preferably the molar ratio of the aryl compound to borane is about 1 to 2.

In particular embodiments of the above amination reactions, the reactions include a base and a second organic ligand. In some embodiments the base is K$_3$PO$_4$ and in some embodiments, the second organic ligand is PtBu$_3$, 2(N,N'-dimethylamino)-2'-dicyclohexylphosphino-1,1'-biphenyl, 2-dicyclohexylphosphino-1,1'-biphenyl, and 2-di-t-butylphosphino-1,1'-biphenyl.

In further embodiments of the above processes for producing the aminoarylboronic ester, the aminoarylboronic ester which is produced is then reacted with an oxidizing compound to replace the boronic ester group with an oxygen.

In further embodiments of the process for producing substituted phenols from an aryl compound, the oxidizing compound is a peroxy compound selected from the group consisting of peroxymonosulfuric acid and salts thereof. In a further embodiment, the oxidizing compound is taken from the group consisting of organic peroxides and salts thereof. In a further embodiment of the above processes, the oxidizing agent is hydrogen peroxide. In a further embodiment of the above processes, the oxidizing compound is an alkali metal peroxymonosulfate, preferably potassium peroxymonosulfate, most preferably 2KHSO$_5$.KHSO$_4$.K$_2$SO$_4$.

OBJECTS

It is an object of the present invention to provide a process for the synthesis of aminoarylboronic esters and substituted anilines from arenes.

DETAILED DESCRIPTION OF THE DRAWINGS

FIG. 1 shows the formulas for precatalysts 1 to 15. Cp* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

Figure 2:
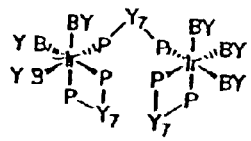
Figure 2:
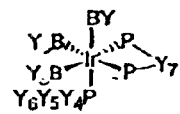
Figure 2:
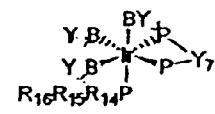
Figure 2:
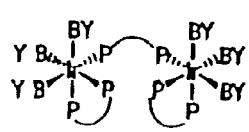
Figure 2:
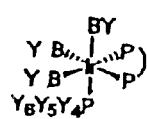
Figure 2:
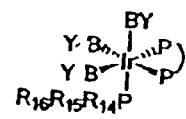
Figure 2:
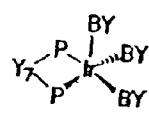
Figure 2:
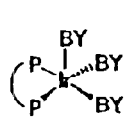
Figure 2:
Figure 2:
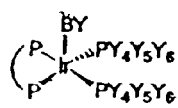
Figure 2:
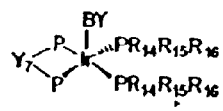
Figure 2:
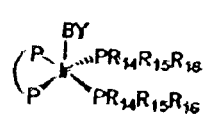

FIG. 2 shows the formulas for precatalysts 16 to 27. $Y_4$, $Y_5$, and $Y_6$ are each selected from the group consisting of hydrogen, halide, alkyl, aryl, alkoxide ($—O(R_{11})$), and amide ($—N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; ($PY_7P$) is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons; (P^P) is of the formula

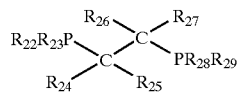

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups; and BY is a boron moiety.

DETAILED DESCRIPTION OF THE INVENTION

All patents, patent applications, provisional patent applications, government publications, government regulations, and literature references cited in this specification are hereby incorporated herein by reference in their entirety. In case of conflict, the present description, including definitions, will control.

The present invention provides a process for producing an aminoarylboronic ester which comprises reacting an aryl compound which is a ring-substituted arene wherein at least one ring substituent is a halogen (aryl halide) or pseudohalogen (e.g., nonaflates and triflates), with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands, preferably under anhydrous conditions, to produce an arylboronic ester; and then aminating the arylboronic ester with an organic compound containing an amine in the presence of a catalytically effective amount of a metal catalyst complex under anhydrous conditions wherein the organic compound is coupled to the aryl group of the arylboronic ester compound to produce the aminoarylboronic ester. The process further includes embodiments wherein the aryl compound is aminated as above and then borylated as above. The process further includes reactions wherein the aryl compound is an aminoaryl compound which is borylated as above.

The process can be performed as a single "one-pot" reaction in a single reaction vessel. Thus, the advantages of the process of the present invention is that it provides direct access to aminoarylboronic acids and esters without need for intermediate purification, isolation, and characterization; thus saving time, expense, money, and reducing hazardous waste, and allows access to aminoarylboronic acids and esters which were previously unknown or difficult/impossible to synthesize using traditional methods. The process of the present invention is particularly useful for pharmaceutical research, commodity chemical producers, specialty chemical manufacturers, and university-based research efforts.

In the first reaction, the B—C bond-forming reaction between a borane and an $sp^2$-hybridized C—H bond of a ring-substituted arene in which at least one of the ring substituents is a halogen or pseudohalogen (aryl compound) to produce an arylboronic ester is catalyzed by a catalyst comprising Ir or Rh in a complex with three or more substituents, preferably excluding hydrogen as a substituent, bonded to the Ir or Rh. In a further embodiment, the reaction includes an organic ligand selected from the group consisting of phosphorus, carbon, nitrogen, oxygen, and sulfur organic ligands. For example, phosphorus organic ligands; nitrogen organic ligands such as pyridine, bipyridines (bpy), trigonal bipyridine (tbpy), and the like; and, organic amines, imines, nitrogen heterocycles, ethers, and the like. Preferably, the ligand to catalyst is in a molar ratio between about 1 to 3 and 3 to 1, preferably 1 to 1, wherein the organic ligand is at least in part bonded to the iridium or rhodium. In general, the ring-substituted arene (aryl compound) has the formula R—Ar—X and the arylboronic ester has the formula

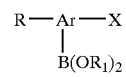

wherein R is any non-interfering group, preferably selected from the group consisting of alkyl, aryl, vinyl, alkoxy, carboxylic esters, amides, cyclic, heteroaryl, heterocyclic, substituted variants thereof, and hydrogen; Ar is any variety of aryl, phenyl, naphthyl, anthracyl, and heteroaryl, and substituted variants thereof; $R_1$ is any non-interfering group, preferably selected from the group consisting of alkyl, aryl, heteroaryl, and substituted variants thereof, and hydrogen; and X is a halogen or pseudohalogen, preferably selected from the group consisting of chlorine, bromine, fluorine, iodine, triflate, and nonaflates. While the precise reaction conditions depend on the substrate, in general, a reaction containing about 2 mol % of the catalyst, about 2 mol % of the ligand, and about 150 mol % of the borane and performed at about 100° to 150° C. for about 2 to 20 hours under anhydrous conditions can be expected to produce the arylboronic ester.

In the second reaction, the C—N bond-forming reaction between the nitrogen of an organic compound comprising a primary or secondary amine and the C—X bond of the arylboronic ester produced above results in the replacement of the halogen with the amine. The reaction is catalyzed by a metal catalytic complex in the presence of a ligand and a base. In a further embodiment, the catalyst comprises palladium. In further embodiments, the base is $K_3PO_4$, preferably anhydrous $K_3PO_4$. The second reaction is performed by adding the amine, metal catalytic complex, ligand, and base (optionally, an organic solvent) to the above reaction containing the arylboronic ester, incubating the reaction under anhydrous conditions at a temperature and a time sufficient to produce the aminoarylboronic ester. While the precise reaction conditions depend on the substrate, in general, a reaction containing about 2 mol % of the metal catalyst and about 140 mol % of the base and performed at about 100° C. for about 10 to 20 hours under anhydrous conditions can be expected to produce the aminoarylboronic ester.

Effective precatalysts for forming the B—C bonds can be grouped into two families: those that contain cyclopentadienyl (Cp*, $C_5R_5$ wherein R is $CH_3$) or indenyl (Ind, $C_9R_7$ wherein R is H) ligands and those that contain phosphine ligands. Included are compounds that contain both the Cp* and the Ind ligands and the phosphine ligands.

Preferably, the Ir catalytic composition for the first step of the process comprises one of the following: $(ArH)Ir(BY)_3$ wherein ArH is selected from the group consisting of aromatic, heteroaromatic, polyaromatic, and heteropolyaromatic hydrocarbon and wherein BY is a boron moiety; $(MesH)Ir(BY)_3$ wherein MesH is mesitylene and wherein BY is a boron moiety; $(P(Y_4)(Y_5)(Y_6))_3Ir(H)_n(BY)_{3-n}$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure, wherein n is 0, 1, or 2, and wherein BY is a boron moiety; $(P(R_{14})(R_{15})(R_{16}))_3Ir(H)_n(BY)_{3-n}$ wherein $R_{14}$, $R_{15}$, and $R_{16}$ are each selected from the group consisting of hydrogen, linear alkyl, branched alkyl, and a carbon in a cyclic structure, wherein n is 0, 1, or 2, and wherein BY is a boron moiety; $(P(Y_4)(Y_5)(Y_6))_3Ir(H)(R_{13})(BY)$ wherein $Y_4$, $Y_5$, and $Y_6$ are as above, wherein $R_{13}$ is selected from the group consisting of a linear alkyl containing 1 to 8 carbon atoms, branched alkyl containing 1 to 8 carbons, aryl, and a carbon in a cyclic structure, and wherein BY is a boron moiety; $(P(R_{14})(R_{15})(R_{16}))_3Ir(H)(R_{17})$ (BY) wherein $R_{14}$, $R_{15}$, and $R_{16}$ are as above; $R_{17}$ is as above, and wherein BY is a boron moiety; $\{(PY_7P)Ir(BY)_3\}_2(\mu_2\text{-}(PY_7P))$ (16) wherein BY is a boron moiety, wherein ($PY_7P$) is $R_{18}R_{19}P\text{—}Y_7\text{—}PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and wherein $Y_7$ is a chain containing 1 to 12 carbons; $(PY_7P)(P(Y_4)(Y_5)(Y_6))Ir(BY)_3$ (17) wherein BY is a boron moiety, wherein $Y_4$, $Y_5$, and $Y_6$ are as above, and wherein ($PY_7P$) is as above; $(PY_7P)(P(R_{10})(R_{11})(R_{12}))Ir(BY)_3$ (18) wherein BY is a boron moiety, wherein $R_{14}$, $R_{15}$, and $R_{16}$ are as above, wherein ($PY_7P$) is as above; $\{(P^{\wedge}P)Ir(BY)_3\}_2(\mu_2\text{-}(P^{\wedge}P))$ (19) wherein BY is a boron moiety and wherein ($P^{\wedge}P$) is of the formula

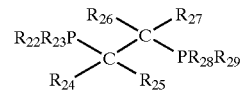

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups; $(P^{\wedge}P)(P(Y_4)(Y_5)(Y_6))Ir(BY)_3$ (20) wherein BY is a boron moiety, wherein $Y_4$, $Y_5$, and $Y_6$ are as above, and wherein ($P^{\wedge}P$) is as above; $(P^{\wedge}P)(P(R_{14})(R_{15})(R_{16}))Ir(BY)_3$ (21) wherein BY is a boron moiety, wherein $R_{14}$, $R_{15}$, and $R_{16}$ are as above, and wherein ($P^{\wedge}P$) is as above; $(PY_7P)Ir(BY)_3$ (22) wherein BY is a boron moiety, and wherein and ($PY_7P$) is as above; $(P^{\wedge}P)Ir(BY)_3$ (23) wherein BY is a boron moiety, and wherein ($P^{\wedge}P$) is as above; $(P(Y_4)(Y_5)(Y_6))_4Ir(BY)$ wherein $Y_4$, $Y_5$, and $Y_6$ are as above and BY is a boron moiety; $(P(R_{14})(R_{15})(R_{16}))_4Ir(BY)$ wherein $R_{14}$, $R_{15}$, and $R_{16}$ are as above and BY is a boron moiety; $(PY_7P)(P(Y_4)(Y_5)(Y_6))_2Ir(BY)$ (24) wherein BY is a boron moiety, wherein $Y_4$, $Y_5$, and $Y_6$ are as above, and wherein ($PY_7P$) is as above; $(P^{\wedge}P)(P(Y_4)(Y_5)(Y_6))_2Ir(BY)$ (25) wherein BY is a boron moiety, wherein $Y_4$, $Y_5$, and $Y_6$ are as above, and wherein ($P^{\wedge}P$) is as above; $(PY_7P)(P(R_{14})(R_{15})(R_{16}))_2Ir(BY)$ (26) wherein BY is a boron moiety, $R_{14}$, $R_{15}$, and $R_{17}$ are as above, and wherein ($PY_7P$) is as above; $(P^{\wedge}P)(P(R_{14})(R_{15})(R_{16}))_2Ir(BY)$ (27) wherein BY is a boron moiety, wherein $R_{14}$, $R_{15}$, and $R_{16}$ are as above, and wherein ($P^{\wedge}P$) is as above.

Examples of catalytic compositions comprising iridium include those selected from the group consisting of ((COD)Ir(OCH$_3$))$_2$, (Cp*)Ir(H)$_2$(Me$_3$P) (1), (Cp*)Ir(H)(BPin)(Me$_3$P)(2), (Cp*)Ir(H)(C$_6$H$_5$)(Me$_3$P) (3), (Ind)Ir(COD)(8), (MesH)Ir(BPin)(B(OR)$_2$)(9), ((R$_1$)$_3$P)$_3$Ir(B(OR$_2$)$_2$)$_3$ (10), (R$_1$)$_2$P)$_2$Ir(BPin)$_3$ (11), (((R$_1$)$_2$P)$_3$Ir((R$_2$O)$_2$B)$_3$)$_2$ (12), ((R$_1$)$_3$ P)$_4$Ir(BPin)(13), ((R$_1$)$_2$P)$_2$Ir(BPin)$_3$ (14), (MesH)Ir(BPin)$_3$ (9 wherein the B(OR)$_2$ is BPin), IrCl(COD)(15), and (IrCl(COD))$_2$, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

Preferably, the Rh catalytic composition for the first step comprises one of the following: $(Cp')(P(Y_4)(Y_5)(Y_6))Rh(H)_n(BY)_{2-n}$ wherein $Y_4$, $Y_5$, and $Y_6$ are as above, wherein n is 0 or 1, wherein BY is a boron moiety, and wherein Cp' is of the formula

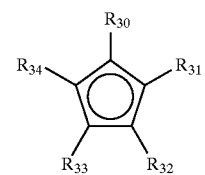

wherein $R_{30}$, $R_{31}$, $R_{32}$, $R_{33}$, and $R_{34}$ are each selected from the group consisting of hydrogen, alkyl chains, carbocyclic rings, and aryl groups; and $(Cp')(P(R_{14}(R_{15})(R_{16}))Rh(H)_n$ $(BY)_{2-n}$ wherein $R_{14}$, $R_{15}$, and $R_{16}$ are as above; n is 0 or 1, wherein BY is a boron moiety; and wherein Cp' is as above.

Examples of catalytic compositions comprising rhodium include those selected from the group consisting of (Cp*)Rh(H)$_2$(Me$_3$P) (4), (Cp*)Rh(H)(BPin)(Me$_3$P) (5), (Cp*)Rh(H)(C$_6$H$_5$)(Me$_3$P)(6), and (Cp*)Rh(hexamethylbenzene)(7), wherein Cp* is 1,2,3,4,5-pentamethylcyclopentadienyl, BPin is pinacolborane, Me is methyl, H is hydrogen, and P is phosphorus.

In the above catalytic compositions, preferably the BY boron moiety selected from the group consisting of

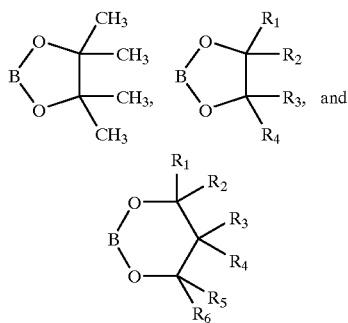

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure. Preferably, the borane is pinacolborane. FIGS. 1 and 2 show the structures of precatalysts 1 to 15 and 16 to 27, respectively.

While the precatalysts can under particular reaction conditions catalyze the borylation of particular ring-substituted arenes, the reactions proceed more efficiently when an organic ligand such as phosphine ligands (phosphorus organic ligands), preferably bidentate phosphine ligands, are included in the reaction mixture. The addition of phosphine ligands to the reaction generates active catalysts which can produce ring-substituted arene boranes (aryl boronate esters and acids) with low catalyst loading. The fact that phosphine-containing species can catalyze borylation is important because numerous phosphines are commercially available. Furthermore, the selectivities of the borylation can be altered as a function of the phosphine ligand that is added. Examples of phosphine ligands include, but are not limited to, trimethyl phosphine (PMe$_3$), 1,2-bis(dimethylphosphino)ethane (dmpe), 1,2-bis(diphenylphosphino)ethane (dppe), Cy$_3$P, and Ph$_3$P. In other embodiments, the ligand can be a nitrogen ligand, preferably a nitrogen ligand selected from the group consisting of 2,2'-dipyridyl and 4,4'-di-tert-butyl-2,2'-dipyridyl.

Examples of catalysts and boron reagents for borylation can be found in commonly owned U.S. application Ser. No. 10/194,809, filed Jul. 12, 2002, and U.S. application Ser. No. 10/194,859, filed Jul. 12, 2002.

Effective catalysts for forming the C—N bond during the amination step of the process are palladium catalyst complexes. Preferably, the palladium catalytic complexes are selected from the group consisting of Pd(PPh$_3$)$_4$, Pd$_2$(dba)$_3$, PdCl$_2$(dppf), and Pd(OAc)$_2$/Cy$_3$P wherein P is phosphorus and Ph is phenyl, dba is dibenzylideneacetone, $^t$Bu is tert-butyl, dppf is diphenylphosphinoferrocene.

The amination reactions proceed more smoothly when a second organic ligand is included in the reaction mixture. Such ligands include, but are not limited to, 2-(N,N'-dimethylamino)-2'-dicyclophosphino-1,1'-biphenyl, tri(tert-butyl)phosphine (PtBu$_3$), 2-dicyclohexylphosphino-1,1'-biphenyl, and 2-di-t-butylphosphino-1,1'-bipheyl.

A typical borylation/amination is performed as follows. An anhydrous mixture containing an aryl compound which is a ring-substituted arene having at least one halogen or pseudohalogen such as triflate or nonaflate, a borane such as HBPin, an iridium or rhodium catalytic complex with three or more substituents such as (Ind)Ir(COD), and a organic ligand selected from the group consisting of phosphorus, carbon, nitrogen, oxygen, and sulfur organic ligands such as dpme is placed in a reaction vessel and stirred. The aryl compound to borane molar ratio in particular embodiments can be from about 10 to 1 to 1 to 10, preferably the molar ratio is about 1 to 2. In particular embodiments, the ratio of catalyst to ligand is about 1 to 1. Thus, as an example, in a typical reaction, the aryl compound is about 2 mmol, the borane is about 2 mmol, the catalyst is about 0.04 mmol, and the ligand is about 0.04 mmol. The reaction vessel is preferably sealed and the mixture stirred from room temperature to 200° C., preferably about 150° C. for a time sufficient to borylate a substantial amount of the aryl compound. Afterwards, the reaction is cooled to room temperature and the reaction then placed under a vacuum for about an hour or passed through a plug of silica.

Next, an organic compound containing an amine moiety, a metal catalyst complex, preferably a Pd catalyst complex such as Pd$_2$dba$_3$, a base such as K$_3$PO$_4$, a ligand such as P(t-Bu)$_3$, and a solvent such as DME are added to the above anhydrous reaction mixture containing the arylboronic ester. The reaction is performed under anhydrous conditions. As an example, a typical reaction containing the above example can then include about 0.02 mmol of the catalyst, about 0.06 mmol of the ligand, about 1.4 to 2.8 mmol of the base, and about 2.40 mmol of the amine moiety. The reaction vessel is sealed and the mixture stirred at a temperature between room temperature and 200° C., preferably 100° C., for a time sufficient to aminate a substantial amount of the arylboronic ester. In general, a reaction time between about 16 to 20 hours would be sufficient. Afterwards, the reaction is cooled and the reaction diluted with a solvent such as Et$_2$O, and then washed with H$_2$O and dried. The solvents can be removed under reduced pressure and column chromatography can be used to purify the aminoarylboronic ester.

It was furthered discovered that under appropriate conditions, a selective amination (Buchwald-Hartwig amination) or Suzuki coupling of an aminoarylboronic ester can be performed using the same Pd-catalyst, base, and solvent used to prepare the aminoarylboronic ester. In the presence of water, it was discovered that Suzuki cross-coupling of an aryl halide with the boronic ester occurs exclusively. However, it was also discovered that when the reaction is run under anhydrous conditions, only the amine functionality reacts with the aryl halide. Scheme 1 illustrates the two reactions: the upper reaction is the Buchwald-Hartwig amination reaction and the lower reaction is the Suzuki coupling reaction.

Scheme 1

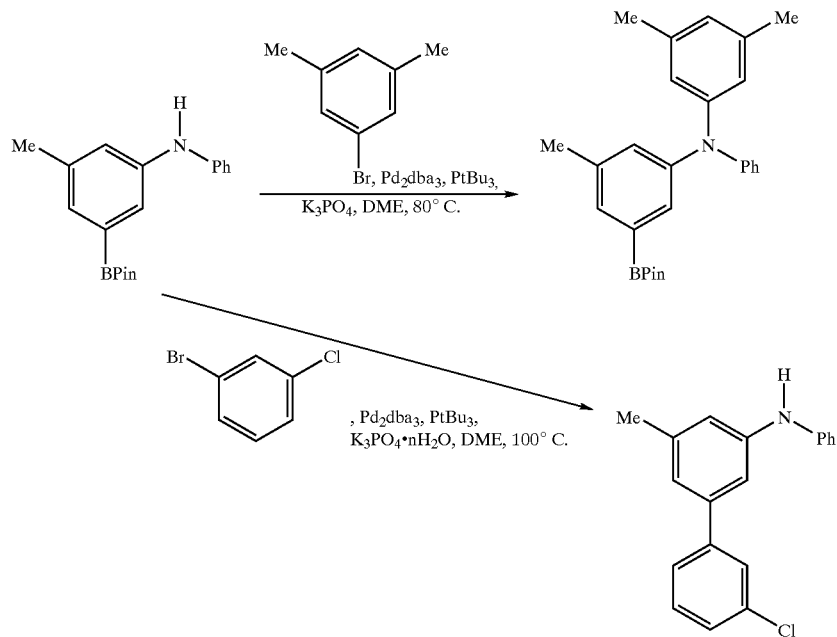

Therefore, once the amino substituted boronic ester has been made via the C—H activation/borylation/amination, that species can be used in a Pd-mediated Suzuki coupling (C—C bond formation) to make biaryls. Methods for making biaryls from arylboronic esters are disclosed in U.S. application Ser. No. 10/194,859, filed Jul. 12, 2002. Alternatively, the same product can be used in a second Pd-mediated Buchwald-Hartwig amination (C—N bond formation). The key to this divergence is whether the reactions are run in the presence of water (C—C formation) or under anhydrous conditions (C—N formation).

Thus, the present invention further provides a two-step, one-pot process for C—N coupling (Buchwald-Hartwig amination) an aryl halide to an aminoarylboronic ester via the amine functionality of the aminoarylboronic ester by reacting the aminoarylboronic ester with the aryl halide in the presence of a palladium metal catalyst complex under anhydrous conditions and provides a two-step, one pot process for C—C coupling (Suzuki coupling) an aryl halide to an aminoarylboronic ester via the borane functionality of the aminoarylboronic ester by reacting the aminoarylboronic ester with the aryl halide in the presence of a palladium metal catalyst complex in the presence of water.

In a further embodiment of the above Buchwald-Hartwig or Suzuki processes, the palladium catalyst complex is selected from the group consisting of $Pd(PPh_3)_4$, $Pd_2(dba)_3$, $PdCl_2(dppf)$, and $Pd(OAc)_2/Cy_3P$ wherein P is phosphorus and Ph is phenyl, dba is dibenzylideneacetone, $^tBu$ is tert-butyl, dppf is diphenylphosphinoferrocene.

In further embodiments of the present invention, the above aminoarylboronic esters can be oxidized to a substituted phenol amine of the general formula $$R-Ar\underset{OH}{|}N\begin{matrix}R_2\\R_3\end{matrix}$$

wherein R, $R_2$, and $R_3$ are each independently an alkyl, aryl, vinyl, alkoxy, carboxylic esters, amides, or halogen and Ar is any variety of phenyl, naphthyl, anthracyl, and heteroaryl. The aminoarylboronic ester produced as above is incubated in the presence of an oxidizing compound such as an alkali metal peroxymonosulfate, preferably potassium peroxymonosulfate, most preferably, $2KHSO_5.KHSO_4.K_2SO_4$ or OXONE (the trademark OXONE is owned by E. I. du Pont de Nemours and Company, Wilmington, Del.), to remove the boronic ester group as shown in Example 4 to produce the substituted phenol amines. Alternatively, the boronic ester group can be replaced by hydrogen. Methods for oxidizing arylboronic esters to substituted phenols are described in U.S. Provisional Patent Application No. 60/397,366, which was filed Jul. 19, 2002. These methods can be used to oxidize aminoarylboronic esters to substituted phenol amines. Other oxidizing compounds include a peroxy compound selected from the group consisting of peroxymonosulfuric acid and salts thereof; organic peroxides and salts thereof such as hydrogen peroxide.

The following examples are intended to promote a further understanding of the present invention.

EXAMPLE 1

This example illustrates the tandem Ir-catalyzed borylation and catalytic amination process.

3-Aminoboronic acids and esters as shown below are of interest as evidenced by the large number of derivatives synthesized, and by several patents, which note their activity as O-lactamase inhibitors (See, for example, Shoichet et al., WO0035905).

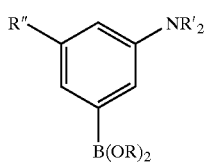

R = H, alkyl, aryl
R' = H, alkyl, aryl, carboxy
R" = H, halo, alkyl, aryl, alkenyl, alkoxy, carboxy, etc.

Few in number, however, are 1,3,5-aminoboronic acids and esters (about 25 compounds by SCIFINDER SCHOLAR). Such substrates may prove useful for further derivatization as they can possess three unique sites for diversity. Furthermore, these compounds may prove ideal as scaffolds for combinatorial libraries. The boronic acid or ester can be transformed into a myriad of functionalities including aryl or vinyl via the Suzuki-Miyuara coupling (Miyaura and Suzuki, Chem. Rev. 95: 2457–2483 (1995); Suzuki, J. Organomet. Chem. 576: 147–168 (1999); Miyaura, In Advances in Metal-Organic Chemistry: Liebeskind, Ed.: JAI: London,; Vol. 6, pp. 187–243 (1998)). If R" is a halogen, then there exists a multitude of coupling opportunities (See, for examples, Metal-catalyzed Cross-coupling Reactions; Diederich and Stang, eds.: Wiley: Wienheim, 1998).

Recently, a catalytic aromatic C—H activation/borylation reaction utilizing Ir- or Rh-catalysts was developed. The process is high yielding, functional group tolerant (alkyl, halo, carboxy, alkoxy, and protected amino), chemoselective (1,3-substited arenes give only the 5-boryl product), and efficient (Iverson and Smith, J. Am. Chem. Soc. 121: 7696–7697 (1999); Cho et al., J. Am. Chem. Soc. 122: 12868–12869 (2000); Tse et al., Org. Lett. 3: 2831 (2001); Chao et al., Science 295: 305–308 (2002)). Furthermore, the process allows for the direct construction of aryl boronic esters from hydrocarbon feedstocks without going through an aryl halide. Scheme 2 depicts a prototypical borylation reaction: borylation of benzene using (Ind)Ir(COD)(2 mol %), dppe (2 mol %).

Scheme 2

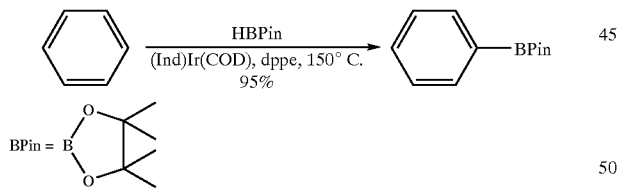

The borane of choice is pinacolborane (HBPin). A variety of Ir(I) catalysts can be used, including [Ir(COD)Cl]$_2$, Ir(Indenyl)(C$_2$H$_4$)$_2$, Ir(Indenyl)dppe, and (Indenyl)Ir(COD), in the presence of 2 mol equivalents of PMe$_3$ or 1 mol equivalent of a bidentate ligand like dmpe or dppe. The catalyst system of choice is (Indenyl)Ir(COD), dppe or dmpe (2 mol % each) because of it's cleanness of reaction and efficient TOF (24 h$^{-1}$ with benzene). The reaction can be run in the neat arene or in inert solvents (e.g. cyclohexane). During our studies into tandem borylation/Suzuki coupling, we noted difficulties with the hydrolysis of the boronic ester functionality (Bpin). The robustness of the BPin group suggested that, perhaps, the pinacol might serve as a protecting group for the boron. Thus, it was deemed of interest to explore other catalytic transformations in the presence of the BPin group. One such transformation is the Buchwald-Hartwig amination of aryl halides (See, for example; Wolfe et al.,. J. Org. Chem. 65: 1158 (2000); Hartwig et al., J. Org. Chem. 64: 5575 (1999); Wolfe and Buchwald, Angew. Chem. Int. Ed. 38: 2413 (1999)). Initially, the reaction was attempted on pure 1-chloro-3-methylphenyl-5-BPin. As shown in Scheme 3 (Buchwald-Hartwig coupling of 1-chloro-3-methylphenyl-5-BPin with aniline), application of Buchwald[]s protocol proceeded cleanly to give the desired cross-coupling product in 64.7% and 63.8% yield. The use of PtBu$_3$ improved the yield to 78.8%. Unfortunately, initial attempts to perform the reaction in the "one-pot" protocol were unsuccessful. Table 1 summarizes the results. In all cases where K$_3$PO$_4$.nH$_2$O was used, a significant amount of pinacol was observed by GC-FID (Entries 1–5). While this is indicative of reaction of the BPin group and is most likely a by-product of Suzuki coupling (in this case, dimerization or oligomerization of the starting material), no dimers or oligiomers were isolated.

Scheme 3

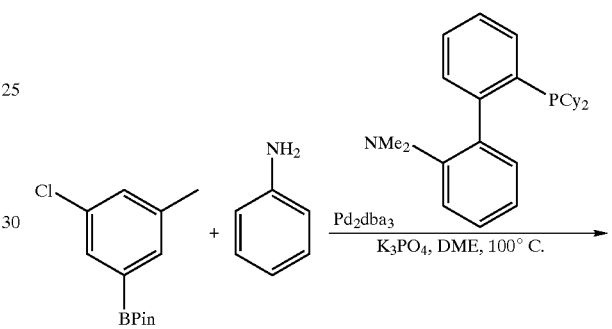

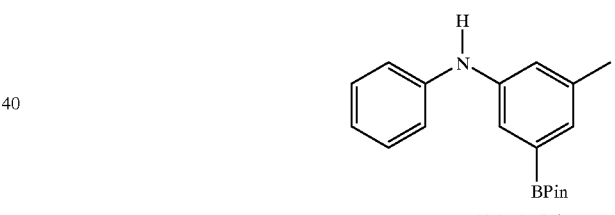

63.8, 64.7%

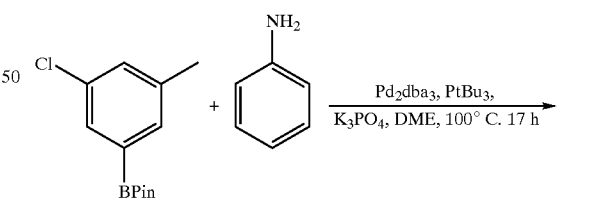

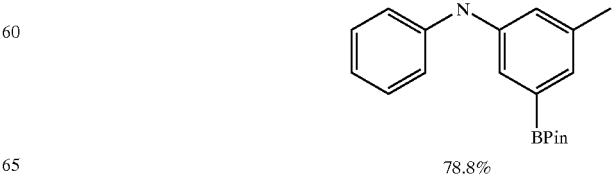

78.8%

TABLE 1

Attempted Buchwald-Hartwig amination of 3-chlorotoluene in tandem catalysis.[a]

| Entry | Mol % Pd Catalyst | Mol % Ligand[e] | Base | H₂NPh | Pinacol | ArCl-BPin | ArCl-NHPh | Ar(NHPh)BPin (meta) | Ar(NHPh)BPin (other) |
|---|---|---|---|---|---|---|---|---|---|
| 1 | 1.0 | 4.0 | K₃PO₄·nH₂O | 70 | 27 | trace | trace | 3 | |
| 2 | 0.5 | 3.0 | K₃PO₄·nH₂O | 69 | 20 | 6 | 0 | 5 | 0 |
| 3 | 1.0 | 4.0 | K₃PO₄·nH₂O | 58 | 14 | 19 | 4 | 5 | 0 |
| 4 | 2.0 | 6.0 PtBu₃ | K₃PO₄·nH₂O | 58 | 15 | 0 | 6 | 11 | 10 |
| 5[b] | 0.5 | 2.0 | K₃PO₄·nH₂O | 65.5 | 25.5 | 0 | 0 | 9 | 0 |
| 6[c] | 0.5 | 2.0 | K₃PO₄ | 35 | 0 | 35 | 4 | 3 | 23 |
| 7[d] | 1.0 | 4.0 | KOtBu | 38 | 0 | 32 | 2 | 19 | 9 |
| 8 | 2.0 | 8.0 | K₃PO₄ | 51 | 0 | 17 | 21 | 3 | 8 |
| 9 | 2.0[d] | 8.0 | K₃PO₄ | 45 | 0 | 53 | 2 | 0 | trace |
| 10[f] | 1.0 | 3.0 | K₃PO₄ | 36 | 0 | 8 | 17 | — | 39 |

[a]Crude ArBPin: obtained from 3-chlorotoluene, 1.5 eq. HBPin, 0.02 eq. (Ind)Ir(COD), 0.02 eq. dppe and was used w/o further purification. Unless otherwise noted, reactions were run with 1.4 eq. base and in DME with 1.2 eq. aniline.
[b]Crude ArBPin passed through a plug of silica prior to use.
[c]Reaction was run for 2 days.
[d]Reaction run in THF.
[e]Ligand was 2-(N,N-dimethylamino)-2'-diphenylphosphino-1,1'-biphenyl.
[f]Run for 4 days. Isolated 34.4% of desired product.

Noteworthy, is the formation of the desired product, albeit in low yield (10% GC-FID ratio), using K₃PO₄·nH₂O and PtBu₃ when all other attempts using the base failed. With anhydrous K₃PO₄, results were better (Entries 6–9). Most importantly, no pinacol was formed in these reactions. Changing the base or increasing catalyst loading did not improve the results. The use of PtBu₃ led to the best results and after 4 days at 100° C., 34.4% of the desired product was isolated (Entry 10). This result, however, falls short of the reaction performed on pure material and shows that the by-products from the Ir-catalyzed borylation are not completely innocuous. As was previously mentioned, a potential source of concern is the presence of free bidentate phosphines after the borylation, which may interfere with subsequent reactions. In the tandem Suzuki reactions, an aryl chloride was successfully coupled only when dmpe was used as the Ir ligand. Thus, the tandem borylation/Buchwald-Hartwig amination reaction of the present invention was attempted using the (Ind)Ir(COD)/dmpe precatalyst. Gratifyingly, this protocol gave the desired aminoaryl boronic ester is an overall yield of 70.8% and 74.8% from 3-chlorotoluene. This one-pot borylation/Buchwald-Hartwig amination process of the present invention is shown in Scheme 4.

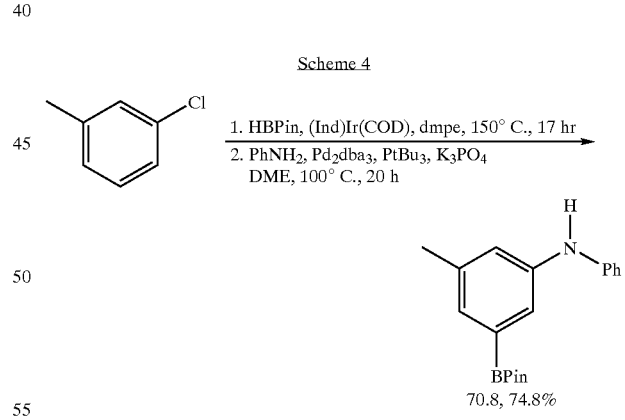

Scheme 4

Again, it was preferable to run the reaction under anhydrous conditions to substantially avoid Suzuki coupling. If one performs the reaction in a stepwise fashion, the overall yield is 60.1%. Thus, it appears that the tandem approach affords the product in significantly better yield. A series of substrates and amines were subjected to the tandem borylation/Buchwald-Hartwig (B—H) amination protocol of the present invention, as shown in Table 2.

TABLE 2

Buchwald-Hartwig amination in tandem catalysis.[a]

1. HBPin, (Ind)Ir(COD), P^P, 100 or 150° C.
2. amine, Pd$_2$dba$_3$, ligand, K$_3$PO$_4$
   DME, 100° C., 17–20 h

| Entry | Substrate | Ir P ligand | Amine | Pd P ligand | Product | % yield |
|---|---|---|---|---|---|---|
| 1 | 3-Cl-C$_6$H$_4$-CF$_3$ | dppe | PhNH$_2$ | 2-PCy$_2$-2'-NMe$_2$-biphenyl | 3-CF$_3$-5-BPin-C$_6$H$_3$-NHPh | 71 / 66.5 / 69.7[b] |
| 2 | 3-Br-toluene | dppe | PhNH$_2$ | 2-PCy$_2$-2'-NMe$_2$-biphenyl | 3-Me-5-BPin-C$_6$H$_3$-NHPh | 46.9 / 47.6 |
| 3 | methyl 3-chlorobenzoate | dppe | PhNH$_2$ | 2-PCy$_2$-2'-NMe$_2$-biphenyl | methyl 3-(PhNH)-5-BPin-benzoate | 47.4 |
| 4 | 3-Cl-toluene | dmpe | morpholine | PtBu$_3$ | 3-Me-5-BPin-C$_6$H$_3$-morpholine | 73.4 |
| 5[c] | methyl 3-chlorobenzoate | dppe | morpholine | 2-PCy$_2$-2'-NMe$_2$-biphenyl | methyl 3-morpholino-5-BPin-benzoate | 43.2 |
| 6[c] | 3-Cl-C$_6$H$_4$-CF$_3$ | dppe | morpholine | 2-PCy$_2$-2'-NMe$_2$-biphenyl | 3-CF$_3$-5-BPin-C$_6$H$_3$-morpholine | 46.3 / 48.9 |

[a]All borylations: 150 mol % HBPin, 2 mol % (Ind)Ir(COD), 2 mol % bidentate phosphine. All aminations: 2 mol % Pd$_2$dba$_3$, 140 mol % K$_3$PO$_4$, DME at 100° C. for 16–20 hours.

TABLE 2-continued

Buchwald-Hartwig amination in tandem catalysis.[a]

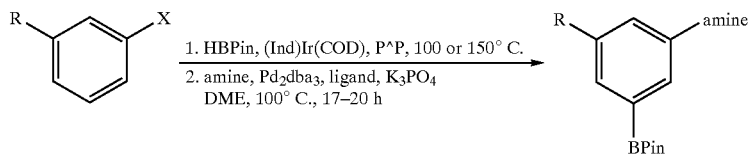

| Entry | Substrate | Ir P ligand | Amine | Pd P ligand | Product | % yield |
|-------|-----------|-------------|-------|-------------|---------|---------|

[b]PtBu$_3$ was used.
[c]Small amounts of aminated dimers were detected.

Thus, both electron-rich and electron-poor haloaryl boronic esters can be aminated in moderate to good yields using this protocol. Thus, for example, borylation of 3-chlorotoluene followed by amination with morpholine using Pd$_2$dba$_3$ and PtBu$_3$ gives the desired aminoaryl boronic ester in 73.4% yield. Borylation of 3-trifluoromethyl toluene followed by amination with aniline using Pd$_2$dba$_3$ with either the Buchwald biaryl phosphine or Hartwig PtBu$_3$ ligand also gives the corresponding aminoaryl boronic ester in good yield (Entry 1; 68.7% for the former and 69.7% for the latter). Contrariwise, amination of the same aryl boronic ester with morpholine was not as successful (Entry 6; 47.6%). For this reaction, a compound (GC-FID ratio to product is 7.7 to 92.3) tentatively identified by GC-MS and $^1$H NMR as the aminated dimer was isolated. The structure of the aminated dimer is

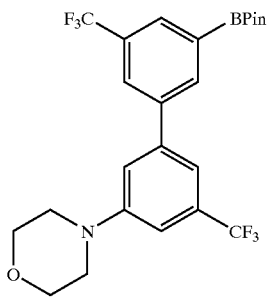

The aminated dimmer is believed to be the result of amine induced Suzuki coupling of the aryl boronic ester with another molecule of itself followed by Pd-catalyzed amination of the remaining chloride group. A similar dimerization was observed for Entry 5 and is presumably formed in a similar manner. As the initialdimer is bifunctional (i.e., it has a chloro and a BPin group), further oligiomerization is likely and thus may account for the poor yield in these cases. The Suzuki coupling is facilitated by electron-poor aryl boronic esters (Entries 1, 3, 5, 6), which will activate the boron towards nucleophilic attack by a base and by a stronger base [protonated pK$_a$ (morpholine)=8.36; pK$_a$ (aniline)=0.78] (Entries 4–6). It is, therefore, likely that the low yields in Table 2 are attributable to competing Suzuki oligiomerization. The successful tandem reaction using (Ind)Ir(COD), dppe for borylation for Entry 1 was somewhat unexpected. Recall that for 3-chlorotoluene, the use of dppe inhibited the subsequent amination. It may simply be that the more activated aryl halides are readily aminated and do not require highly active Pd-catalysts.

While this coupling is remarkable, the usefulness of the products for further transformations could be called in question. In particular, could the boronic ester functionality be coupled to give an aminobiaryl (Scheme 1, lower reaction) or would the amine undergo Buchwald-Hartwig amination to give a trisubstituted amine (Scheme 1, upper reaction). To address this issue, pure 1-N-phenyl-3-methylphenylboronic ester was subjected to coupling with 3-chlorobromobenzene. Gratifyingly, the desired biaryl was obtained in 69% yield. In addition to the selectivity of the coupling, the product would not be easily accessible following an alternative route; namely, Suzuki coupling followed by amination because there would be an issue as to which chloro group would be functionalized.

EXAMPLE 2

Tandem Synthesis of N-phenyl-3-BPin-5-methylaniline.

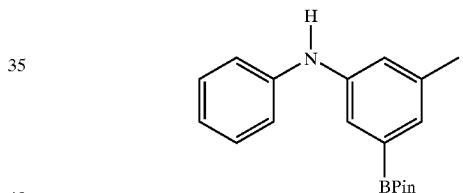

To an airfree flask equipped with a stir bar, in a glove box, was added 3-chlorotoluene (253 mg, 2.00 mmol), HBPin (512 mg, 4.00 mmol), (Ind)Ir(COD)(16.6 mg, 0.04 mmol), dmpe (6.0 mg, 0.04 mmol). The flask was sealed, removed for the glove box, and stirred at 150° C. for 17 h. The reaction mixture was allowed to cool to room temperature and subsequently placed under vacuum for ~1 h. The air free flask was brought into the dry box and Pd$_2$dba$_3$ (18.3 mg, 0.02 mmol), P(t-Bu)$_3$ (12.1 mg, 0.06 mmol), K$_3$PO$_4$ (594 mg, 2.8 mmol), aniline (224 mg, 2.41 mmol), and DME (3 mL) were added. Sealed, removed from dry box, and stirred at 100° C. for 19 h. Cooled, diluted with Et$_2$O, washed with H$_2$O (3×30 ml), dried with MgSO$_4$, and removed solvents under reduced pressure. Column chromatography eluting with hexanes:CH$_2$Cl$_2$ (2:3) gave 462.8 mg (74.8%) of the desired product as a light yellow oil. mp=100° C. $^1$H NMR (CDCl$_3$, 500 MHz) δ 7.59 (d, J=2.0 Hz, 1H), 7.56 (br s, 1H), 7.07–7.03 (m, 2H), 6.92–6.89 (m, 2H), 6.86 (br s, 1H), 6.77–6.74 (m, 1H). $^{13}$C NMR (CDCl$_3$, 75 MHz) δ 144.0, 143.0, 138.4, 129.5, 129.1, 122.4, 122.2, 120.7, 117.8, 83.66, 24.94, 21.34. $^{11}$B NMR (C$_6$D$_6$, 96 Hz) δ 29.12. FT-IR (NaCl) 3393, 3365 (sh), 3036, 2979, 2926, 2867, 1590, 1518, 1497, 1470, 1410, 1368, 1312, 1271, 1237, 1215, 1167, 1144, 1117, 1031, 1019, 967, 911, 853, 745, 712, 698, 668 cm$^{-1}$. GC-MS retention time=17.94 min. MS (% rel. int.): m/z 309 (100), 294 (2), 250 (3), 236 (7), 209 (27), 193

(14), 167 (11), 147 (5). Anal. Calcd for $C_{19}H_{24}BO_2N$: C, 73.80; H, 7.82; N, 4.53. Found: C, 73.82; H, 7.94; N, 4.43.

EXAMPLE 3

A process for producing substituted phenol amines from aminoarylboronic esters is provided.

An aminoarylboronic ester is prepared as in any one of the above examples and then oxidized to its corresponding phenol using one of the four conditions shown below.

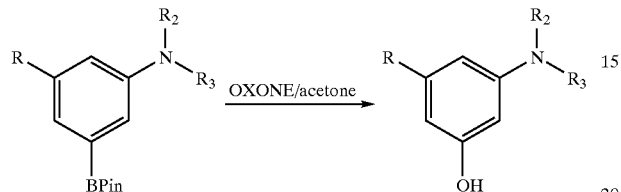

Oxidation condition A is as follows. A mixture prepared as above containing the aminoarylboronic ester is placed in an air free flask and is vigorously stirred. To this mixture is added 1.5 mL 1.5 M aqueous NaOH, followed by 5 min stirring. Then 0.73 g $NaHCO_3$ is added followed by 4.7 ml acetone. The mixture is cooled by an ice bath, and 3.2 mL 0.33 M aqueous OXONE is added slowly. After 12–15 min of stirring, the reaction is quenched by $NaHSO_3$.

Oxidation condition B (no $NaHCO_3$) is as follows. A mixture prepared as above containing the aminoarylboronic ester is placed in an air free flask and is vigorously stirred. To this mixture is added 1.5 mL 1.5 M aqueous NaOH, followed by 5 min stirring. Then 4.7 ml acetone is added. The mixture is then cooled by an ice bath, and 3.2 mL 0.33 M aqueous OXONE is added slowly. After 12–15 min of stirring, the reaction is quenched by $NaHSO_3$.

Oxidation condition C (no NaOH) is as follows. A mixture prepared as above containing the aminoarylboronic ester is placed in an air free flask and is vigorously stirred. To this mixture is added 3.0–3.5 ml acetone and 3–5 min are allowed to stir. The mixture is then cooled by an ice bath, and 3.2 mL 0.33 M aqueous OXONE is added slowly. After 12–15 min of stirring, the reaction is quenched by $NaHSO_3$.

Oxidation condition D (no ice bath) is as follows. A mixture prepared as above containing the aminoarylboronic ester is placed in an air free flask and is vigorously stirred. To this mixture is added 3.0–3.5 ml acetone and 3–5 min are allowed to stir. Then 3.2 mL 0.33 M aqueous OXONE is added dropwise at room temperature. After 7 min of stirring, the reaction is quenched by $NaHSO_3$.

In the oxidation, the preferred acetone/water ratio is about 1:1. While other solvents can be used in the oxidation, acetone is presently the preferred solvent. The phenol can be prepared by column chromatography or sublimation.

EXAMPLE 4

Alternative process for producing aminoarylboronic acids and esters, which are more lengthy or more limited in scope. Below are two such processes (Schemes 5 and 6):

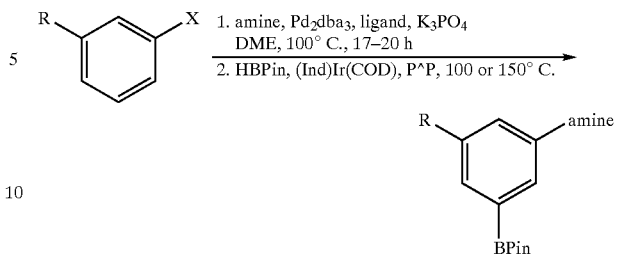

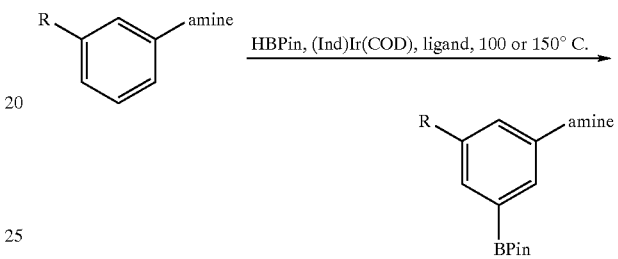

For primary amines and arylamines, borylation may in some cases prove problematic. For other amines, borylation may in some cases proceed very slowly. Therefore, the above processes are possible as well.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for producing an aminoarylboronic ester which comprises:
    (a) reacting an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands under anhydrous conditions to produce an arylboronic ester; and
    (b) aminating the arylboronic ester with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester.

2. The process of claim 1 wherein the iridium complex is selected from the group consisting of $((COD)Ir(OCH_3))_2$, $(Cp*)Ir(H)_2$ $(Me_3P)$, $(Cp*)Ir(H)(BPin)(Me_3P)$, $(Cp*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B)_3)_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

3. The process of claim 1 wherein the iridium complex is (Ind)Ir(COD) wherein Ind is indenyl and COD is 1,5-cyclooctadiene.

4. The process of claim 1 wherein the iridium complex is $((COD)Ir(OCH_3))_2$ wherein COD is 1,5-cyclooctadiene.

5. The process of claim 1 wherein the organic ligand is a phosphorus organic ligand selected from the group consisting of trimethyl phosphine ($PMe_3$), 1,2-bis(dimethylphosphino)ethane (dmpe), and 1,2-bis(diphenylphosphino)ethane (dppe).

6. The process of claim 1 wherein the organic ligand is a nitrogen ligand selected from the group consisting of 2,2'-dipyridyl and 4,4'-di-tert-butyl-2,2'-dipyridyl.

7. The process of claim 1 wherein the borane is pinacolborane (BPin).

8. The process of claim 1 wherein the metal catalyst is palladium.

9. The process of claim 1 wherein the metal catalyst complex is selected from the group consisting of $Pd(PPh_3)_4$, $pd_2(dba)_3$, $Pd_2(dba)_3/P(^tBu)_3$, $PdCl_2(dppf)$, and $Pd(OAc)_2/Cy_3P$ wherein P is phosphorus and Ph is phenyl, dba is dibenzylideneacetone, $^tBu$ is tert-butyl, dppf is diphenylphosphinoferrocene.

10. The process of claim 1 wherein the aryl compound has the formula (R)Ar(X), the arylboronic ester has the formula $(R)Ar(X)B(OR_1)$, and the aminoarylboronic ester has the formula $(R)Ar(NR_2R_3)B(OR_1)_2$ wherein R, $R_2$, and $R_3$ are each selected from the group consisting of alkyl, aryl, vinyl, alkoxy, carboxylic esters, amides, and halogen; Ar is selected from the group consisting of phenyl, naphthyl, anthracyl, and heteroaryl; X is selected from the group consisting of chloro, bromo, iodo, triflates, and nonaflates; and $R_1$ is selected from the group consisting of alkyl, hydrogen, and aryl.

11. The process of claim 1 wherein the aminoarylboronic ester is reacted with an oxidizing compound to remove the boronic ester group.

12. The process of claim 1 wherein the molar ratio of the aryl compound to the borane is between about 10 to 1 and 1 to 10.

13. The process of claim 1 wherein the molar ratio of the aryl compound to borane is about 1 to 2.

14. The process of claim 1 wherein the amination includes a base and a second organic ligand.

15. The process of claim 14 wherein the base is $K_3PO_4$.

16. The process of claim 14 wherein the second organic ligand is selected from the group consisting of $PtBu_3$, 2-(N,N'-dimethylamino)-2'-dicyclophosphino-1,1'-biphenyl, 2-dicyclohexylphosphino-1,1'-biphenyl, and 2-di-t-butylphosphino-1,1'-bipheyl.

17. A process for producing an aminoarylboronic ester which comprises:
(a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands under anhydrous conditions to produce an arylboronic ester; and
(b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester.

18. The process of claim 17 wherein the iridium complex is selected from the group consisting of $((COD)Ir(OCH_3))_2$, $(Cp^*)Ir(H)_2(Me_3P)$, $(Cp^*)Ir(H)(BPin)(Me_3P)$, $(Cp^*)Ir(H)(C_6H_5)(Me_3P)$, (Ind)Ir(COD), (Ind)Ir(dppe), $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B)_3)_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein $Cp^*$ is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

19. The process of claim 17 wherein the iridium complex is (Ind)Ir(COD) wherein Ind is indenyl and COD is 1,5-cyclooctadiene.

20. The process of claim 17 wherein the iridium complex is $((COD)Ir(OCH_3))_2$ wherein COD is 1,5-cyclooctadiene.

21. The process of claim 17 wherein the organic ligand is a phosphorus organic ligand selected from the group consisting of trimethyl phosphine ($PMe_3$), 1,2-bis(dimethylphosphino)ethane (dmpe), and 1,2-bis(diphenylphosphino)ethane (dppe).

22. The process of claim 17 wherein the organic ligand is a nitrogen ligand selected from the group consisting of 2,2'-dipyridyl and 4,4'-di-tert-butyl-2,2'-dipyridyl.

23. The process of claim 17 wherein the borane is pinacolborane (BPin).

24. The process of claim 17 wherein the metal catalyst is palladium.

25. The process of claim 17 wherein the metal catalyst complex is selected from the group consisting of $Pd(PPh_3)_4$, $pd_2(dba)_3$, $Pd_2(dba)_3/P(^tBu)_3$, $PdCl_2(dppf)$, and $Pd(OAc)_2/Cy_3P$ wherein P is phosphorus and Ph is phenyl, dba is dibenzylideneacetone, $^tBu$ is tert-butyl, dppf is diphenylphosphinoferrocene.

26. The process of claim 17 wherein the aryl compound has the formula (R)Ar(X), the arylboronic ester has the formula $(R)Ar(X)B(OR_1)$, and the aminoarylboronic ester has the formula $(R)Ar(NR_2R_3)B(OR_1)_2$ wherein R, $R_2$, and $R_3$ are each selected from the group consisting of alkyl, aryl, vinyl, alkoxy, carboxylic esters, amides, and halogen; Ar is selected from the group consisting of phenyl, naphthyl, anthracyl, and heteroaryl; X is selected from the group consisting of chloro, bromo, iodo, triflates, and nonaflates; and $R_1$ is selected from the group consisting of alkyl, hydrogen, and aryl.

27. The process of claim 17 wherein the aminoarylboronic ester is reacted with an oxidizing compound to replace the boronic ester group with oxygen.

28. The process of claim 17 wherein the molar ratio of the aryl compound to the borane is between about 10 to 1 and 1 to 10.

29. The process of claim 17 wherein the molar ratio of the aryl compound to borane is about 1 to 2.

30. The process of claim 17 wherein the amination includes a base and a second organic ligand.

31. The process of claim 30 wherein the base is $K_3PO_4$.

32. The process of claim 30 wherein the second organic ligand is selected from the group consisting of $PtBu_3$, 2-(N,N'-dimethylamino)-2'-dicyclophosphino-1,1'- biphenyl, 2-dicyclohexylphosphino-1,1'-biphenyl, and 2-di-t-butylphosphino-1,1'-bipheyl.

33. A process for C—N coupling an aryl halide to an aminoarylboronic ester via the amine functionality of the aminoarylboronic ester which comprises:
   (a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands under anhydrous conditions to produce an arylboronic ester;
   (b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester; and
   (c) reacting the aminoarylboronic ester with the aryl halide in the presence of a palladium metal catalyst complex under anhydrous conditions to couple the aryl halide to the amine functionality of the aminoarylboronic ester.

34. The process of claim 33 wherein the iridium complex is selected from the group consisting of $((COD)Ir(OCH_3))_2$, $(Cp^*)Ir(H)_2$ $(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B)_3)_2$, $(R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

35. The process of claim 33 wherein the iridium complex is (Ind)Ir(COD) wherein Ind is indenyl and COD is 1,5-cyclooctadiene.

36. The process of claim 33 wherein the iridium complex is $((COD)Ir(OCH_3))_2$ wherein COD is 1,5-cyclooctadiene.

37. The process of claim 33 wherein the organic ligand is a phosphorus organic ligand selected from the group consisting of trimethyl phosphine ($PMe_3$), 1,2-bis(dimethylphosphino)ethane (dmpe), and 1,2-bis(diphenylphosphino)ethane (dppe).

38. The process of claim 33 wherein the organic ligand is a nitrogen ligand selected from the group consisting of 2,2'-dipyridyl and 4,4'-di-tert-butyl-2,2'-dipyridyl.

39. The process of claim 33 wherein the borane is pinacolborane (BPin).

40. The process of claim 33 wherein the metal catalyst is palladium.

41. The process of claim 33 wherein the metal catalyst complex is selected from the group consisting of $Pd(PPh_3)_4$, $Pd_2(dba)_3$, $Pd_2(dba)_3/P(^tBu)_3$, $PdCl_2(dppf)$, and $Pd(OAc)_2/Cy_3P$ wherein P is phosphorus and Ph is phenyl, dba is dibenzylideneacetone, $^tBu$ is tert-butyl, dppf is diphenylphosphinoferrocene.

42. The process of claim 33 wherein the aryl compound has the formula (R)Ar(X), the arylboronic ester has the formula $(R)Ar(X)B(OR_1)$, and the aminoarylboronic ester has the formula $(R)Ar(NR_2R_3)B(OR_1)_2$ wherein R, $R_2$, and $R_3$ are each selected from the group consisting of alkyl, aryl, vinyl, alkoxy, carboxylic esters, amides, and halogen; Ar is selected from the group consisting of phenyl, naphthyl, anthracyl, and heteroaryl; X is selected from the group consisting of chloro, bromo, iodo, triflates, and nonaflates; and $R_1$ is selected from the group consisting of alkyl, hydrogen, and aryl.

43. The process of claim 33 wherein the molar ratio of the aryl compound to the borane is between about 10 to 1 and 1 to 10.

44. The process of claim 33 wherein the molar ratio of the aryl compound to borane is about 1 to 2.

45. The process of claim 33 wherein the amination includes a base and a second organic ligand.

46. The process of claim 45 wherein the base is $K_3PO_4$.

47. The process of claim 45 wherein the second organic ligand is selected from the group consisting of $PtBu_3$, 2-(N,N'-dimethylamino)-2'-dicyclophosphino-1,1'-biphenyl, 2-dicyclohexylphosphino-1,1'-biphenyl, and 2-di-t-butylphosphino-1,1'-bipheyl.

48. A process for C—C coupling an aryl halide to an aminoarylboronic ester via the borane functionality of the aminoarylboronic ester which comprises:
   (a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands under anhydrous conditions to produce an arylboronic ester;
   (b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester; and
   (c) reacting the aminoarylboronic ester with the aryl halide in the presence of a palladium metal catalyst complex in the presence of water to couple the aryl halide to the aminoarylboronic ester.

49. The process of claim 48 wherein the iridium complex is selected from the group consisting of $((COD)Ir(OCH_3))_2$, $(Cp^*)Ir(H)_2(Me_3P)$, $(Cp^*)Ir(H)(BPin)(Me_3P)$, $(Cp^*)Ir(H)(C_6H_5)(Me_3P)$, $(Ind)Ir(COD)$, $(Ind)Ir(dppe)$, $(MesH)Ir(BPin)(B(OR)_2)_2$, $((R_1)_3P)_3Ir(B(OR_2)_2)_3$, $(R_1)_2P)_2Ir(BPin)_3$, $(((R_1)_2P)_3Ir((R_2O)_2B)_3)_2$, $((R_1)_3P)_4Ir(BPin)$, $((R_1)_3P)_2Ir(BPin)_3$, $(MesH)Ir(BPin)_3$, and $(IrCl(COD))_2$, $(PMe_3)_2IrH_5$, $((R_1)_3P)_2IrH_5$, and $((R)_3P)_2IrH_x(B(OR_2)_2)_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are hydrogen, linear or branched alkyl containing 1 to 8 carbons, aryl, or a carbon in a cyclic structure.

50. The process of claim 48 wherein the iridium complex is (Ind)Ir(COD) wherein Ind is indenyl and COD is 1,5-cyclooctadiene.

51. The process of claim 48 wherein the iridium complex is $((COD)Ir(OCH_3))_2$ wherein COD is 1,5-cyclooctadiene.

52. The process of claim 48 wherein the organic ligand is a phosphorus organic ligand selected from the group consisting of trimethyl phosphine ($PMe_3$), 1,2-bis(dimethylphosphino)ethane (dmpe), and 1,2-bis(diphenylphosphino)ethane (dppe).

53. The process of claim 48 wherein the organic ligand is a nitrogen ligand selected from the group consisting of 2,2'-dipyridyl and 4,4'-di-tert-butyl-2,2'-dipyridyl.

54. The process of claim 48 wherein the borane is pinacolborane (BPin).

55. The process of claim 48 wherein the metal catalyst is palladium.

56. The process of claim 48 wherein the metal catalyst complex is selected from the group consisting of Pd(PPh$_3$)$_4$, pd$_2$(dba)$_3$, Pd$_2$(dba)$_3$/P($^t$Bu)$_3$, PdCl$_2$(dppf), and Pd(OAc)$_2$/Cy$_3$P wherein P is phosphorus and Ph is phenyl, dba is dibenzylideneacetone, $^t$Bu is tert-butyl, dppf is diphenylphosphinoferrocene.

57. The process of claim 48 wherein the aryl compound has the formula (R)Ar(X), the arylboronic ester has the formula (R)Ar(X)B(OR$_1$), and the aminoarylboronic ester has the formula (R)Ar(NR$_2$R$_3$)B(OR$_1$)$_2$ wherein R, R$_2$, and R$_3$ are each selected from the group consisting of alkyl, aryl, vinyl, alkoxy, carboxylic esters, amides, and halogen; Ar is selected from the group consisting of phenyl, naphthyl, anthracyl, and heteroaryl; X is selected from the group consisting of chloro, bromo, iodo, triflates, and nonaflates; and R$_1$ is selected from the group consisting of alkyl, hydrogen, and aryl.

58. The process of claim 48 wherein the molar ratio of the aryl compound to the borane is between about 10 to 1 and 1 to 10.

59. The process of claim 48 wherein the molar ratio of the aryl compound to borane is about 1 to 2.

60. The process of claim 48 wherein the amination includes a base and a second organic ligand.

61. The process of claim 60 wherein the base is K$_3$PO$_4$.

62. The process of claim 60 wherein the second organic ligand is selected from the group consisting of PtBu$_3$, 2-(N,N'-dimethylamino)-2'-dicyclophosphino-1,1'-biphenyl, 2-dicyclohexylphosphino-1,1'-biphenyl, and 2-di-t-butylphosphino-1,1'-bipheyl.

63. A process for producing an aminoarylboronic ester which comprises:

reacting an arylboronic ester with an organic compound containing an amine moiety in the presence of a catalytically effective amount of a metal catalyst complex under anhydrous conditions wherein the organic compound is coupled to the aryl group of the arylboronic ester compound to produce the aminoarylboronic ester.

64. The process of claim 63 wherein the borane of the arylboronic ester is pinacolborane (BPin).

65. The process of claim 63 wherein the metal catalyst is palladium.

66. The process of claim 63 wherein the metal catalyst complex is selected from the group consisting of Pd(PPh$_3$)$_4$, Pd$_2$(dba)$_3$, Pd$_2$(dba)$_3$/P($^t$Bu)$_3$, PdCl$_2$(dppf), and Pd(OAc)$_2$/Cy$_3$P wherein P is phosphorus and Ph is phenyl, dba is dibenzylideneacetone, $^t$Bu is tert-butyl, dppf is diphenylphosphinoferrocene.

67. The process of claim 63 wherein the arylboronic ester has the formula (R)Ar(X)B(OR$_1$) and the aminoarylboronic ester has the formula (R)Ar(NR$_2$R$_3$)B(OR$_1$)$_2$ wherein R, R$_2$, and R$_3$ are each selected from the group consisting of alkyl, aryl, vinyl, alkoxy, carboxylic esters, amides, and halogen; Ar is selected from the group consisting of phenyl, naphthyl, anthracyl, and heteroaryl; X is selected from the group consisting of chloro, bromo, iodo, triflates, and nonaflates; and R$_1$ is selected from the group consisting of alkyl, hydrogen, and aryl.

68. The process of claim 63 wherein the aminoarylboronic ester is reacted with an oxidizing compound to replace the boronic ester group with an oxygen.

69. The process of claim 63 wherein the reaction includes a base and a second organic ligand.

70. The process of claim 69 wherein the base is K$_3$PO$_4$.

71. The process of claim 69 wherein the second organic ligand is selected from the group consisting of PtBu$_3$, 2-(N,N'-dimethylamino)-2'-dicyclophosphino-1,1'-biphenyl, 2-dicyclohexylphosphino-1,1'-biphenyl, and 2-di-t-butylphosphino-1,1'-bipheyl.

72. A process for producing a substituted phenol amine which comprises:

(a) reacting in a reaction vessel an aryl compound with a borane selected from the group consisting of a borane with a B—H, B—B, and B—Si bond in the presence of a catalytically effective amount of an iridium or rhodium complex with three or more substituents, and an organic ligand selected from the group consisting of phosphorus, carbon, nitrogen, oxygen, and sulfur organic ligands under anhydrous conditions to produce an arylboronic ester;

(b) aminating the arylboronic ester formed in the reaction vessel with an organic compound containing an amine moiety in the presence of a catalytically effective amount of a metal catalyst complex under anhydrous conditions wherein the organic compound is coupled to the aryl group of the arylboronic ester compound to produce an aminoarylboronic ester; and (c) oxidizing the aminoarylboronic ester with a hydrogenating oxidizing compound to produce the substituted phenol amine.

73. The process of claim 72 wherein the oxidizing compound is a peroxy compound selected from the group consisting of peroxymonosulfuric acid and salts thereof.

74. The process of claim 72 wherein the oxidizing compound is an alkali metal peroxymonosulfate.

75. The process of claim 74 wherein the alkali metal peroxymonosulfate is potassium peroxymonosulfate.

76. The process of claim 72 wherein the oxidizing compound is 2KHSO$_5$.KHSO$_4$.K$_2$SO$_4$.

77. The process of claim 72 wherein the oxidizing compound is an organic peroxide.

78. The process of claim 72 wherein the oxidizing compound is hydrogen peroxide.

79. The process of claim 72 wherein the iridium complex is selected from the group consisting of ((COD)Ir(OCH$_3$))$_2$, (Cp*)Ir(H)$_2$(Me$_3$P), (Cp*)Ir(H)(BPin)(Me$_3$P), (Cp*)Ir(H)(C$_6$H$_5$)(Me$_3$P), (Ind)Ir(COD), (Ind)Ir(dppe), (MesH)Ir(BPin)(B(OR)$_2$)$_2$, ((R$_1$)$_3$P)$_3$Ir(B(OR$_2$)$_2$)$_3$, (R$_1$)$_2$P)$_2$Ir(BPin)$_3$, (((R$_1$)$_2$P)$_3$Ir((R$_2$O)$_2$B)$_3$)$_2$, ((R$_1$)$_2$P)$_4$Ir(BPin), ((R$_1$)$_3$P)$_2$Ir(BPin)$_3$, (MesH)Ir(BPin)$_3$, and (IrCl(COD))$_2$, (PMe$_3$)$_2$IrH$_5$, ((R$_1$)$_3$P)$_2$IrH$_5$, and ((R)$_3$P)$_2$IrH$_x$(B(OR$_2$)$_2$)$_{5-x}$ where x is 0–4, wherein Cp* is 1,2,3,4,5-pentamethylcyclopentadienyl, BPin is pinacolborane, Me is methyl, H is hydrogen, P is phosphorus, Ind is indenyl, COD is 1,5-cyclooctadiene, MesH is mesitylene, and wherein R, R$_1$, and R$_2$ are hydrogen, linear or branched alkyl containing 1 to 8 carbons, aryl, or a carbon in a cyclic structure.

80. The process of claim 72 wherein the iridium complex is (Ind)Ir(COD) wherein Ind is indenyl and COD is 1,5-cyclooctadiene.

81. The process of claim 72 wherein the iridium complex is ((COD)Ir(OCH$_3$))$_2$ wherein COD is 1,5-cyclooctadiene.

82. The process of claim 72 wherein the organic ligand is a phosphorus organic ligand selected from the group consisting of trimethyl phosphine (PMe$_3$), 1,2-bis(dimethylphosphino)ethane (dmpe), and 1,2-bis(diphenylphosphino)ethane (dppe).

83. The process of claim 72 wherein the organic ligand is a nitrogen ligand selected from the group consisting of 2,2'-dipyridyl and 4,4'-di-tert-butyl-2,2'-dipyridyl.

84. The process of claim 72 wherein the borane is pinacolborane (BPin).

85. The process of claim 72 wherein the metal catalyst is palladium.

86. The process of claim 72 wherein the metal catalyst complex is selected from the group consisting of Pd(PPh$_3$)$_4$, pd$_2$(dba)$_3$, Pd$_2$(dba)$_3$/P($^t$Bu)$_3$, PdCl$_2$(dppf), and Pd(OAc)$_2$/Cy$_3$P wherein P is phosphorus and Ph is phenyl, dba is dibenzylideneacetone, $^t$Bu is tert-butyl, dppf is diphenylphosphinoferrocene.

87. The process of claim 72 wherein the aryl compound has the formula (R)Ar(X), the arylboronic ester has the formula (R)Ar(X)B(OR$_1$), and the aminoarylboronic ester has the formula (R)Ar(NR$_2$R$_3$)B(OR$_1$)$_2$ wherein R, R$_2$, and R$_3$ are each selected from the group consisting of alkyl, aryl, vinyl, alkoxy, carboxylic esters, amides, and halogen; Ar is selected from the group consisting of phenyl, naphthyl, anthracyl, and heteroaryl; X is selected from the group consisting of chloro, bromo, iodo, triflates, and nonaflates; and R$_1$ is selected from the group consisting of alkyl, hydrogen, and aryl.

88. The process of claim 72 wherein the molar ratio of the aryl compound to the borane is between about 10 to 1 and 1 to 10.

89. The process of claim 72 wherein the molar ratio of the aryl compound to borane is about 1 to 2.

90. The process of claim 72 wherein the amination includes a base and a second organic ligand.

91. The process of claim 90 wherein the base is K$_3$PO$_4$.

92. The process of claim 90 wherein the second organic ligand is selected from the group consisting of PtBu$_3$, 2-(N,N'-dimethylamino)-2'-dicyclophosphino-1,1'-biphenyl, 2-dicyclohexylphosphino-1,1'-biphenyl, and 2-di-t-butylphosphino-1,1'-bipheyl.

* * * * *

UNITED STATES PATENT AND TRADEMARK OFFICE
CERTIFICATE OF CORRECTION

| | | |
|---|---|---|
| PATENT NO. | : 6,958,420 B2 | |
| DATED | : October 25, 2005 | |
| INVENTOR(S) | : Robert E. Maleczka, Jr., Milton R. Smith, III and Danial Holmes | |

It is certified that error appears in the above-identified patent and that said Letters Patent is hereby corrected as shown below:

<u>Column 10,</u>
Line 6, "1,1'-bipheyl." should be -- 1,1'-biphenyl --.
Line 54, "It was furthered discovered" should be -- It was further discovered --.

<u>Column 13,</u>
Line 19, "Suzuki-Miyura coupling" should be -- Suzuki-Miyaura coupling --.
Line 32, "1,3-substited arenes" should be -- 1,3-substituted arenes --.

<u>Column 14,</u>
Line 9, "Buchwald[]s" should be -- Buchwald's --.

<u>Column 15,</u>
Line 63, "ester is an overall" should be -- ester an overall --.

<u>Column 19,</u>
Line 51, "As the initialdimer is" should be -- As the initial dimer is --.

<u>Column 20,</u>
Line 46, "for the glove" should be -- from the glove --.

<u>Column 23,</u>
Line 54, "1,1'-bipheyl." should be -- 1,1'-biphenyl --.

<u>Column 25,</u>
Line 2, "1,1'-bipheyl." should be -- 1,1'-biphenyl --.
Line 32, ")$_2$,(R$_1$)$_3$P)$_4$Ir" should be -- )$_2$,((R$_1$)$_3$P)$_4$Ir --.

<u>Column 26,</u>
Line 19, "1,1'-bipheyl." should be -- 1,1'-biphenyl --.

<u>Column 27,</u>
Line 36, "1,1'-bipheyl." should be -- 1,1'-biphenyl --.

<u>Column 28,</u>
Line 8, "1,1'-bipheyl." should be -- 1,1'-biphenyl --.

UNITED STATES PATENT AND TRADEMARK OFFICE
CERTIFICATE OF CORRECTION

PATENT NO.    : 6,958,420 B2
DATED         : October 25, 2005
INVENTOR(S)   : Robert E. Maleczka, Jr., Milton R. Smith, III and Danial Holmes It is certified that error appears in the above-identified patent and that said Letters Patent is hereby corrected as shown below:

Column 30,
Line 16, "1,1'-bipheyl." should be -- 1,1'-biphenyl --.

Signed and Sealed this

Twenty-eighth Day of February, 2006

JON W. DUDAS
*Director of the United States Patent and Trademark Office*